(12) United States Patent
Kapadia

(10) Patent No.: US 12,029,507 B2
(45) Date of Patent: Jul. 9, 2024

(54) SURGICAL ROBOTIC SYSTEMS

(71) Applicant: Covidien LP, Mansfield, MA (US)

(72) Inventor: Jaimeen Kapadia, Cambridge, MA (US)

(73) Assignee: COVIDIEN LP, Mansfield, MA (US)

( * ) Notice: Subject to any disclaimer, the term of this patent is extended or adjusted under 35 U.S.C. 154(b) by 808 days.

(21) Appl. No.: 17/263,070

(22) PCT Filed: Jul. 17, 2019

(86) PCT No.: PCT/US2019/042112
§ 371 (c)(1),
(2) Date: Jan. 25, 2021

(87) PCT Pub. No.: WO2020/023255
PCT Pub. Date: Jan. 30, 2020

(65) Prior Publication Data
US 2021/0169591 A1  Jun. 10, 2021

Related U.S. Application Data

(60) Provisional application No. 62/703,489, filed on Jul. 26, 2018.

(51) Int. Cl.
*A61B 34/30* (2016.01)
*A61B 90/50* (2016.01)
(Continued)

(52) U.S. Cl.
CPC .............. *A61B 34/30* (2016.02); *A61B 90/50* (2016.02); *A61B 34/25* (2016.02); *A61B 34/37* (2016.02); *A61B 34/71* (2016.02); *A61B 34/74* (2016.02)

(58) Field of Classification Search
CPC ......... A61B 34/30; A61B 90/50; A61B 34/25; A61B 34/37; A61B 34/71; A61B 34/74; A61B 2017/00477; A61B 2017/00991
See application file for complete search history.

(56) References Cited

U.S. PATENT DOCUMENTS

| 2,957,353 A | 10/1960 | Babacz |
| 3,111,328 A | 11/1963 | Di Rito et al. |

(Continued)

FOREIGN PATENT DOCUMENTS

| CA | 2451558 A1 | 1/2003 |
| CN | 1547454 A | 11/2004 |

(Continued)

OTHER PUBLICATIONS

Supplemental Partial European Search Report dated Apr. 8, 2022, issued in corresponding EP Appln. No. 19840043, 13 pages.

(Continued)

*Primary Examiner* — Victor L Macarthur
(74) *Attorney, Agent, or Firm* — Carter, DeLuca & Farrell, LLP

(57) ABSTRACT

A surgical robotic system includes an elongated slide, a carriage for supporting an instrument drive unit, a drive motor operably coupled to the carriage and configured to drive a movement of the carriage relative to the slide, and a motor release mechanism configured to selectively disengage the drive motor from the carriage to permit a manual movement of the carriage along the slide.

17 Claims, 11 Drawing Sheets

(51) Int. Cl.
*A61B 34/00* (2016.01)
*A61B 34/37* (2016.01)

(56) References Cited

U.S. PATENT DOCUMENTS

| | | | |
|---|---|---|---|
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,683,772 A | 8/1987 | Colimitra |
| 4,705,038 A | 11/1987 | Sjostrom et al. |
| 4,722,685 A | 2/1988 | de Estrada et al. |
| 4,823,807 A | 4/1989 | Russell et al. |
| 4,862,759 A | 9/1989 | Trevelyan et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,784,542 A | 7/1998 | Ohm et al. |
| 5,792,573 A | 8/1998 | Pitzen et al. |
| 5,797,536 A | 8/1998 | Smith et al. |
| 5,797,900 A | 8/1998 | Madhani et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,451,027 B1 | 9/2002 | Cooper et al. |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,554,844 B2 | 4/2003 | Lee et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |

(56) References Cited

U.S. PATENT DOCUMENTS

| | | |
|---|---|---|
| 7,422,139 B2 | 9/2008 | Shelton, IV et al. |
| 7,422,592 B2 | 9/2008 | Morley et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,074,859 B2 | 12/2011 | Kostrzewski |
| 8,092,451 B2 | 1/2012 | Schechter et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,237,388 B2 | 8/2012 | Jinno et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,465,476 B2 | 6/2013 | Rogers et al. |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,192 B2 | 1/2014 | Farascioni et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,925,786 B2 | 1/2015 | Holsten et al. |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 8,998,799 B2 | 4/2015 | Orban, III et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,937,626 B2 | 4/2018 | Rockrohr |
| 10,179,413 B2 | 1/2019 | Rockrohr |

(56) References Cited

U.S. PATENT DOCUMENTS

| | | |
|---|---|---|
| 2001/0031975 A1 | 10/2001 | Whitman et al. |
| 2002/0040217 A1 | 4/2002 | Jinno |
| 2002/0049454 A1 | 4/2002 | Whitman et al. |
| 2002/0087148 A1 | 7/2002 | Brock et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0079884 A1 | 4/2006 | Manzo et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0235436 A1 | 10/2006 | Anderson et al. |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0039256 A1 | 2/2008 | Jinno et al. |
| 2008/0058801 A1 | 3/2008 | Taylor et al. |
| 2008/0103491 A1 | 5/2008 | Omori et al. |
| 2008/0109012 A1 | 5/2008 | Falco et al. |
| 2008/0110958 A1 | 5/2008 | McKenna et al. |
| 2008/0119870 A1 | 5/2008 | Williams |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0196533 A1* | 8/2008 | Bergamasco .......... B25J 9/0072 901/29 |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0245175 A1 | 10/2008 | Jinno et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0016852 A1 | 1/2010 | Manzo et al. |
| 2010/0016853 A1 | 1/2010 | Burbank |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0228264 A1 | 9/2010 | Robinson et al. |
| 2010/0292708 A1 | 11/2010 | Madhani et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0010616 A1 | 1/2012 | Huang et al. |
| 2012/0074199 A1 | 3/2012 | Olson et al. |
| 2012/0080475 A1 | 4/2012 | Smith et al. |
| 2012/0080485 A1 | 4/2012 | Woodard, Jr. et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0116416 A1 | 5/2012 | Neff et al. |
| 2012/0143002 A1 | 6/2012 | Aranyi et al. |
| 2012/0168485 A1 | 7/2012 | Marczyk et al. |
| 2012/0172924 A1 | 7/2012 | Allen, IV |
| 2012/0199630 A1 | 8/2012 | Shelton, IV |
| 2012/0209292 A1* | 8/2012 | Devengenzo .......... A61B 34/30 606/130 |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0020376 A1 | 1/2013 | Shelton, IV et al. |
| 2013/0032629 A1 | 2/2013 | Viola |
| 2013/0093149 A1 | 4/2013 | Saur et al. |
| 2013/0131695 A1 | 5/2013 | Scarfogliero et al. |
| 2013/0158542 A1 | 6/2013 | Manzo et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0325095 A1 | 12/2013 | Ollivier |
| 2013/0331858 A1 | 12/2013 | Devengenzo et al. |
| 2013/0334281 A1 | 12/2013 | Williams |
| 2014/0005640 A1 | 1/2014 | Shelton, IV et al. |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0166023 A1 | 6/2014 | Kishi |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |

(56) References Cited

U.S. PATENT DOCUMENTS

| | | |
|---|---|---|
| 2014/0378761 A1 | 12/2014 | Zorn et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0150636 A1 | 6/2015 | Hagn et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2017/0142738 A1 | 5/2017 | You et al. |
| 2018/0168748 A1 | 6/2018 | Kapadia |

FOREIGN PATENT DOCUMENTS

| | | |
|---|---|---|
| CN | 1957854 A | 5/2007 |
| CN | 101340852 A | 1/2009 |
| CN | 101495046 A | 7/2009 |
| CN | 102058437 A | 5/2011 |
| CN | 102247182 A | 11/2011 |
| CN | 103732174 A | 4/2014 |
| CN | 104394793 A | 3/2015 |
| CN | 104619280 A | 5/2015 |
| CN | 105611894 A | 5/2016 |
| DE | 102008053842 A1 | 5/2010 |
| EP | 0443576 A1 | 8/1991 |
| EP | 0705571 A1 | 4/1996 |
| EP | 1563793 A1 | 8/2005 |
| EP | 1769754 A1 | 4/2007 |
| EP | 2316345 A1 | 5/2011 |
| EP | 2668910 A2 | 12/2013 |
| EP | 3416582 A1 | 12/2018 |
| ES | 2333509 A1 | 2/2010 |
| JP | 2005125075 A | 5/2005 |
| JP | 2009226028 A | 10/2009 |
| JP | 2012120884 A | 6/2012 |
| JP | 2013034833 A | 2/2013 |
| JP | 2013103137 A | 5/2013 |
| JP | 2014512888 A | 5/2014 |
| JP | 2015134203 A | 7/2015 |
| KR | 20120022521 A | 3/2012 |
| WO | 2011016640 A2 | 2/2011 |
| WO | 2011037394 A3 | 8/2011 |
| WO | 2011108840 A2 | 9/2011 |
| WO | 2012/040984 A1 | 4/2012 |
| WO | 2015023834 A1 | 2/2015 |
| WO | 2015142785 A1 | 9/2015 |
| WO | 2016043845 A1 | 3/2016 |
| WO | 2017142738 A1 | 8/2017 |
| WO | 2017151458 A1 | 9/2017 |
| WO | 2018013304 A1 | 1/2018 |

OTHER PUBLICATIONS

Extended European Search Report dated Jul. 12, 2022, issued in corresponding EP Appln. No. 19840043, 12 pages.

Openbuilds: "V-Slot Linear Actuator Bundle (Belt Driven) Example Build", Oct. 8, 2015, XP093107956, Avaialble at:https://www.youtube.com/watch?v=eCr1 ogUuNPA, Last retrieved on Jan. 5, 2024.

Examination Report Issued in European Patent Application No. 19 840 043.4 dated Dec. 6, 2023 (8 pages).

Chinese Office Action Dated Dec. 4, 2023 for Chinese Application No. 2019800603387 (12 pages).

\* cited by examiner

SURGICAL ROBOTIC SYSTEMS

CROSS-REFERENCE TO RELATED APPLICATIONS

This application is a U.S. National Stage Application filed under 35 U.S.C. § 371(a) of International Patent Application Serial No. PCT/US2019/042112, filed Jul. 17, 2019, which claims the benefit of and priority to U.S. Provisional Patent Application Ser. No. 62/703,489, filed Jul. 26, 2018, the entire disclosure of which is incorporated by reference herein.

BACKGROUND

Surgical robotic systems have been used in minimally invasive medical procedures. Some surgical robotic systems included a console supporting a surgical robotic arm and a surgical instrument having at least one end effector (e.g., forceps or a grasping tool) mounted to the robotic arm. The robotic arm provided mechanical power to the surgical instrument for its operation and movement.

Manually-operated surgical instruments often included a handle assembly for actuating the functions of the surgical instrument. However, when using a robotic surgical system, no handle assembly was typically present to actuate the functions of the end effector. Accordingly, to use each unique surgical instrument with a robotic surgical system, an instrument drive unit was used to interface with the selected surgical instrument to drive operations of the surgical instrument.

The instrument drive unit was typically coupled to the robotic arm via a slide. The slide allowed the instrument drive unit and the attached surgical instrument to move along an axis of the slide, providing a means for adjusting the axial position of the end effector of the surgical instrument relative to a patient.

SUMMARY

In accordance with an aspect of the present disclosure, a surgical robotic system is provided and includes an elongated slide defining a longitudinal axis, a carriage for supporting an instrument drive unit, a drive motor, and a motor release mechanism. The carriage is coupled to the slide and movable relative thereto along the longitudinal axis. The drive motor is operably coupled to the carriage and configured to drive the movement of the carriage relative to the slide. The motor release mechanism is configured to selectively disengage the drive motor from the carriage to permit a manual movement of the carriage along the slide.

In aspects, the system may further include a pulley that operably couples the drive motor and the carriage. An activation of the motor release mechanism may disengage the pulley from the drive motor.

In certain aspects, the system may further include a motor output member rotatable by the drive motor. An activation of the motor release mechanism may slide the pulley relative to the motor output member from a first position to a second position. In the first position, the pulley and the motor output member are rotatable with one another, and in the second position the pulley is independently rotatable relative to the motor output member.

The system may further include a torque transfer pin non-rotatably coupling the pulley with the motor output member. The pulley may be configured to slide between the first and second positions along the torque transfer pin.

In aspects, the system may further include a one way bearing disposed between the pulley and the motor output member. The one way bearing may be configured to allow rotation of the pulley relative to the motor output member in a first direction, and resist rotation of the pulley relative to the motor output member in a second direction.

The one way bearing may be disposed within the pulley, and the motor output member may extend through the one way bearing and the pulley.

In certain aspects, the one way bearing may be non-rotationally fixed to the motor output member.

In aspects, the motor release mechanism may include a hub axially retained with the pulley and threadedly coupled to the motor output member. A rotation of the hub may move the pulley relative to the motor output member between the first and second positions.

The motor release mechanism may further include a knob configured to slide into and out of non-rotatable engagement with the hub.

In aspects, the system may further include a belt operably coupled to the pulley and fixed to the carriage, such that movement of the belt drives a movement of the carriage along the side.

The system may further include a robotic arm having the slide coupled thereto.

In another aspect of the present disclosure, a surgical robotic system includes a robotic arm, an elongated slide coupled to an end portion of the robotic arm, a drive motor, a pulley, and a motor release mechanism. The pulley is operably coupled to the drive motor and configured to drive a movement of an instrument drive unit along the slide. The motor release mechanism is configured to selectively disengage the pulley from the drive motor to permit a manual rotation of the pulley relative to the drive motor.

The system may further include a belt operably coupled to the pulley and fixedly coupled to an instrument drive unit, such that movement of the belt drives a movement of an instrument drive unit along the side.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
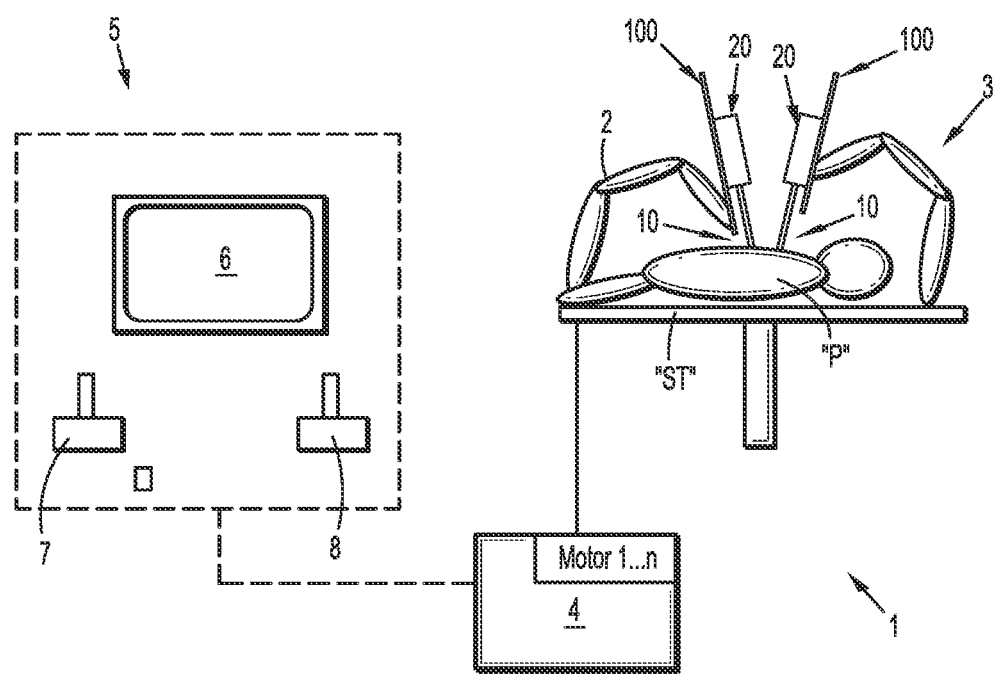
FIG. 1 is a schematic illustration of a surgical robotic system including an instrument drive unit coupled to a slide in accordance with the present disclosure.
Figure 2:
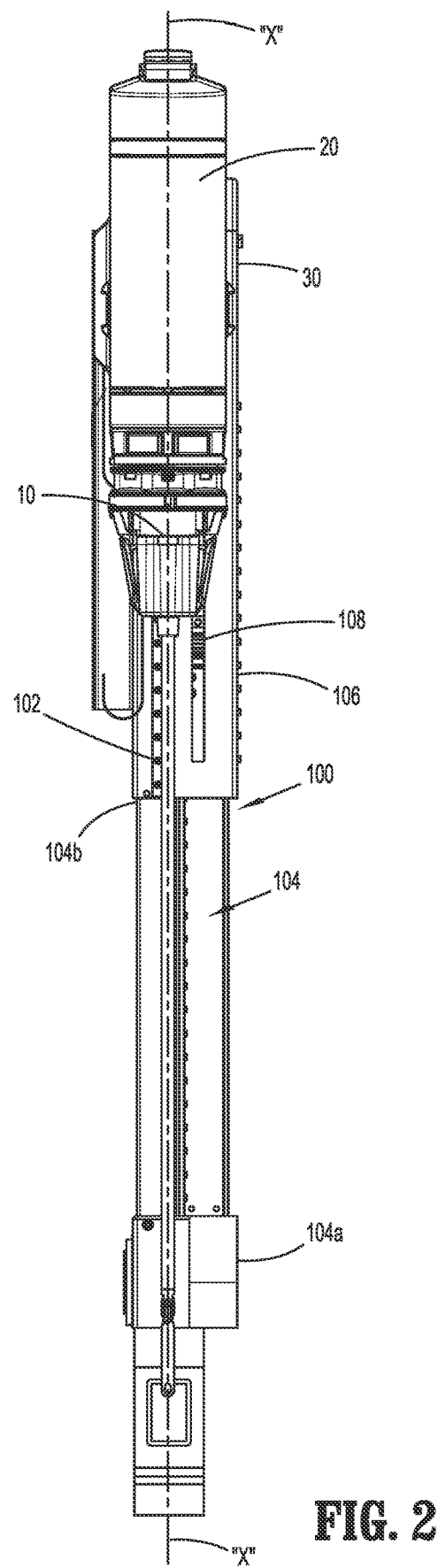
FIG. 2 is a front view of the instrument drive unit and an associated surgical instrument coupled to an exemplary embodiment of a slide.

Embodiments of the presently disclosed surgical robotic system and methods of use thereof are described in detail with reference to the drawings, in which like reference numerals designate identical or corresponding elements in each of the several views. As used herein, the term "proximal" refers to that portion of the surgical robotic system or component thereof that is closest to the clinician, while the term "distal" refers to that portion of the surgical robotic system or component thereof further from the clinician.

As will be described in detail below, provided is a surgical robotic system including a robotic arm, an elongated slide or rail coupled to the robotic arm, a belt and pulley system for driving movement of an instrument drive unit along the slide, and a motor release mechanism for selectively disengaging the belt and pulley system from a drive motor. During an emergency (e.g., a power outage), the motor release mechanism may be activated to allow for manual movement of the instrument drive unit along the slide. The motor release mechanism includes a one way bearing that allows for manual movement of the instrument drive unit in the direction away from a patient and resists manual movement of the instrument drive unit in a direction toward the patient.

Referring initially to FIG. 1, a surgical system, such as, for example, a surgical robotic system 1, generally includes a plurality of surgical robotic arms 2, 3 having an instrument drive unit 20 and an electromechanical instrument 10 removably attached thereto; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art.

Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, the attached instrument drive units 20, and thus electromechanical instrument 10 execute a desired movement according to a movement defined by means of manual input devices 7, 8. Control device 4 may also be set up in such a way that it regulates the movement of robotic arms 2, 3 and/or of the drives.

Surgical robotic system 1 is configured for use on a patient "P" lying on a surgical table "ST" to be treated in a minimally invasive manner by means of a surgical instrument, e.g., electromechanical instrument 10. Surgical robotic system 1 may also include more than two robotic arms 2, 3, the additional robotic arms likewise being connected to control device 4 and being telemanipulatable by means of operating console 5. A surgical instrument, for example, an electromechanical surgical instrument 10 (including an electromechanical end effector (not shown)), may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control a plurality of motors (not explicitly shown) of instrument drive unit 20 to drive various operations of surgical instrument 10. The instrument drive unit 20 transfers power and actuation forces from its motors to driven members (not shown) of the electromechanical instrument 10 to ultimately drive movement of components of the end effector (not shown) of the electromechanical instrument 10, for example, a movement of a knife blade (not shown) and/or a closing and opening of jaw members (not shown) of the end effector.

For a more detailed description of the construction and operation of components of an exemplary robotic surgical system, reference may be made to U.S. Pat. No. 8,828,023, entitled "Medical Workstation," (hereinafter, "the '023 patent"), and International Patent Publication WO2017/205308A1, entitled "Robotic Surgical Assemblies," filed on May 23, 2017, (hereinafter, "the '308 Publication"), the entire contents of each of which are incorporated by reference herein.

With reference to FIGS. 2-7, the surgical robotic system 1 includes a carriage 30 on which the instrument drive unit 20 is supported or carried, and the slide 100, which supports the carriage 30. The carriage 30 is configured to fix the instrument drive unit 20 thereto, such that movement of the carriage 30 along and relative to the slide 100 causes the instrument drive unit 20 to move therewith. The carriage 30 is slidably coupled to a linear track 102 defined longitudinally along an outer sleeve 106 of the slide 100, as will be described below.

The slide 100 may have a generally rectangular shape and is constructed from an inner shaft 104 and an outer sleeve or sheath 106 disposed around the inner shaft 104. In embodiments, the slide 100 may assume any suitable shape, such as, for example, tubular or cylindrical. The inner shaft 104 is coupled to an end of the robotic arm 2 (FIG. 1) either in a fixed or rotatable manner. The inner shaft 104 has a bottom end portion 140a and a top end portion 104b and defines a longitudinal axis "X" therebetween. The inner shaft 104 may have an overall length approximately equal to half the length of a conventional slide.

Figure 3:
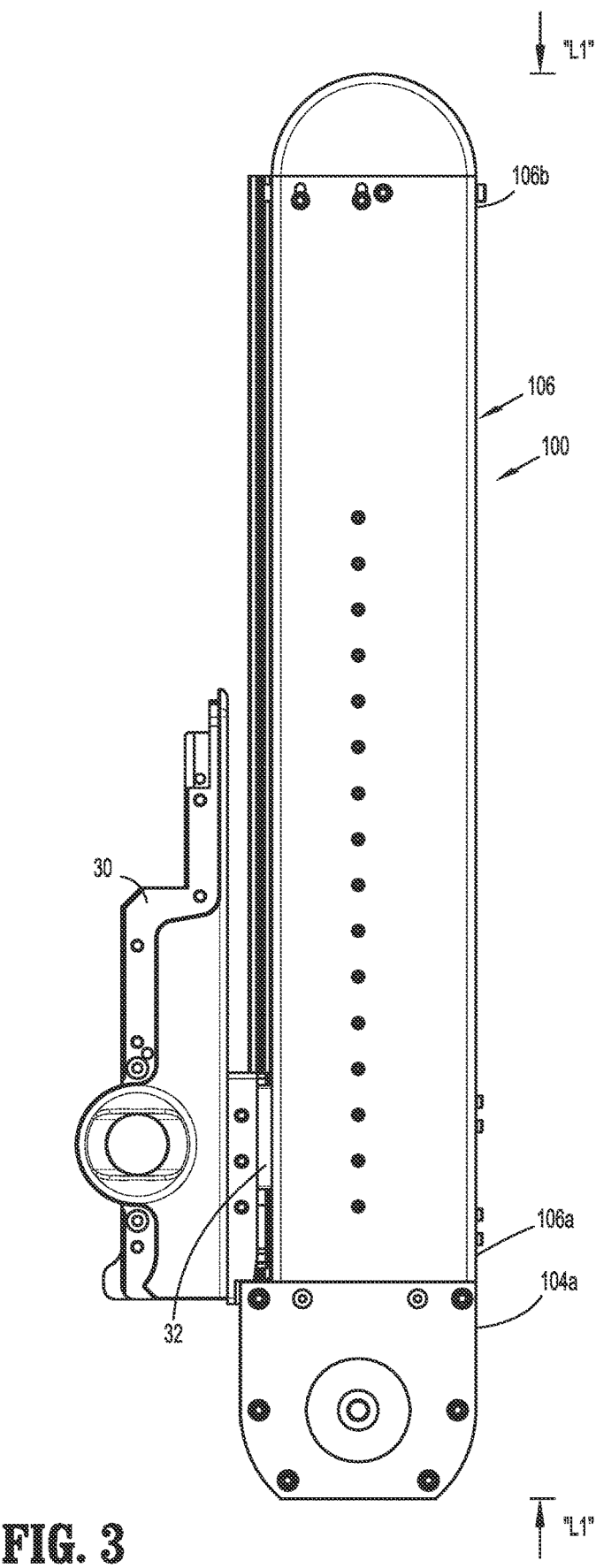
FIG. 3 is a side view, with parts removed, of a carriage coupled to the slide of FIG. 2.
Figure 7:
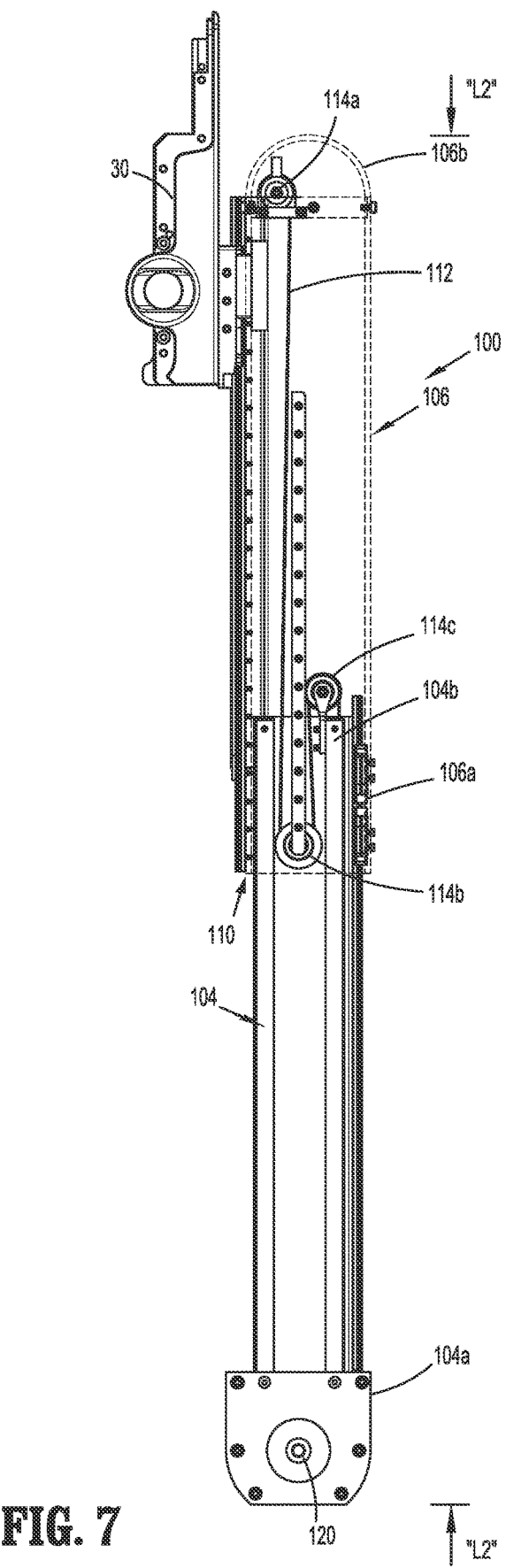
FIG. 7 is a side perspective view, with parts removed, of the carriage coupled to the slide, illustrating the slide in an extended configuration and the carriage in an ascended position.
Figure 8:
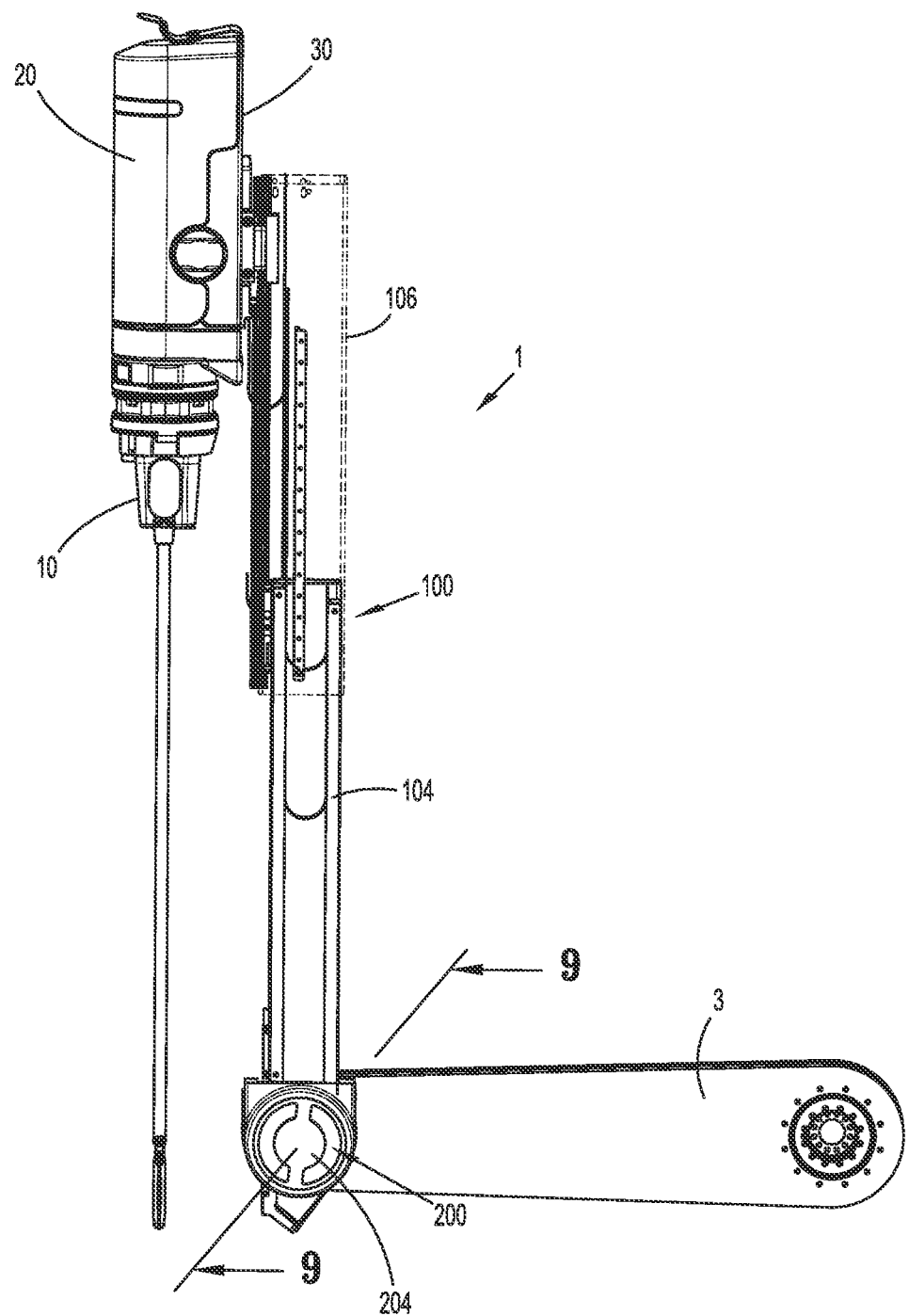
FIG. 8 is a perspective view of the slide coupled to a portion of a robotic arm, illustrating a motor release mechanism for use with the belt and pulley system of FIG. 6.

The outer sleeve 106 of the slide 100 is disposed about the inner shaft 104 and is telescopically coupled thereto. As such, the outer sleeve 106 is slidable along and relative to the longitudinal axis "X" of the inner shaft 104 between a retracted position, as shown in FIG. 3, and an extended position, as shown in FIG. 7. When the outer sleeve 106 is in the retracted position, the slide has a first length "L1" (FIG. 3), substantially equal to approximately half the length of a conventional slide (e.g., as shown and described in the '023 patent, and the '308 Publication), and when the outer sleeve is in the extended position, the slide 100 has a second length "L2" (FIG. 7), substantially equal to approximately the full length of a conventional slide.

The outer sleeve 106 of the slide 100 defines a longitudinally-extending track 102. The track 102 of the outer sleeve 106 may be a single rail or a pair of parallel rails. As mentioned above, the carriage 30 is slidably coupled to the track 102 of the outer sleeve 106. More specifically, the carriage 30 has a coupling member or flange 32 extending from a back side thereof and through an elongated slot 108 of the outer sleeve 106. The coupling member 32 of the carriage 30 is received in an interior chamber 110 (FIG. 7) of the outer sleeve 106 and is fixed to a belt or cable 112 of a belt and pulley system 114 of the slide 100 for driving the movement of the carriage 30 between the ascended and descended positions, as will be described in detail.

The elongated slot 108 is defined along the length of the outer sleeve 106 and runs parallel with the track 102 between a bottom end portion 106a of the outer sleeve 106 and a top end portion 106b of the outer sleeve 106. The elongated slot 108 of the outer sleeve 106 has an upper limit defining a surface feature 116 that prevents the carriage 30 from ascending beyond the upper limit. In embodiments, the surface feature 116 may be a projection extending outwardly from the top end portion 106b of the outer sleeve 106. Upon the coupling member 32 of the carriage 30 contacting the surface feature 116, a threshold force exerted on the carriage 30 in an upward direction causes the outer sleeve 106 to rise relative to the inner shaft 104.

The top end portion 106b may further include a locking feature 118, such as, for example, a roller catch, a magnetic latch, or the like. The locking feature 118 is configured to selectively lock the carriage 30 to the top end portion 106b of the outer sleeve 106 when the carriage 30 enters the ascended position. As such, with the outer sleeve 106 in the extended position relative to the inner shaft 104, as shown in FIG. 7, a downward force exerted on the carriage 30 via the belt 112 causes the outer sleeve 106 to move downwardly with the carriage 30 due to the locking feature 118 locking the outer sleeve 106 and the carriage 30 to one another. Upon the bottom end portion 106a of the outer sleeve 106 bottoming out on the bottom end portion 104a of the inner shaft 104, the locking feature 118 releases the carriage 30 to allow the carriage 30 to descend along the track 102 of the outer sleeve 106.

Figure 5:
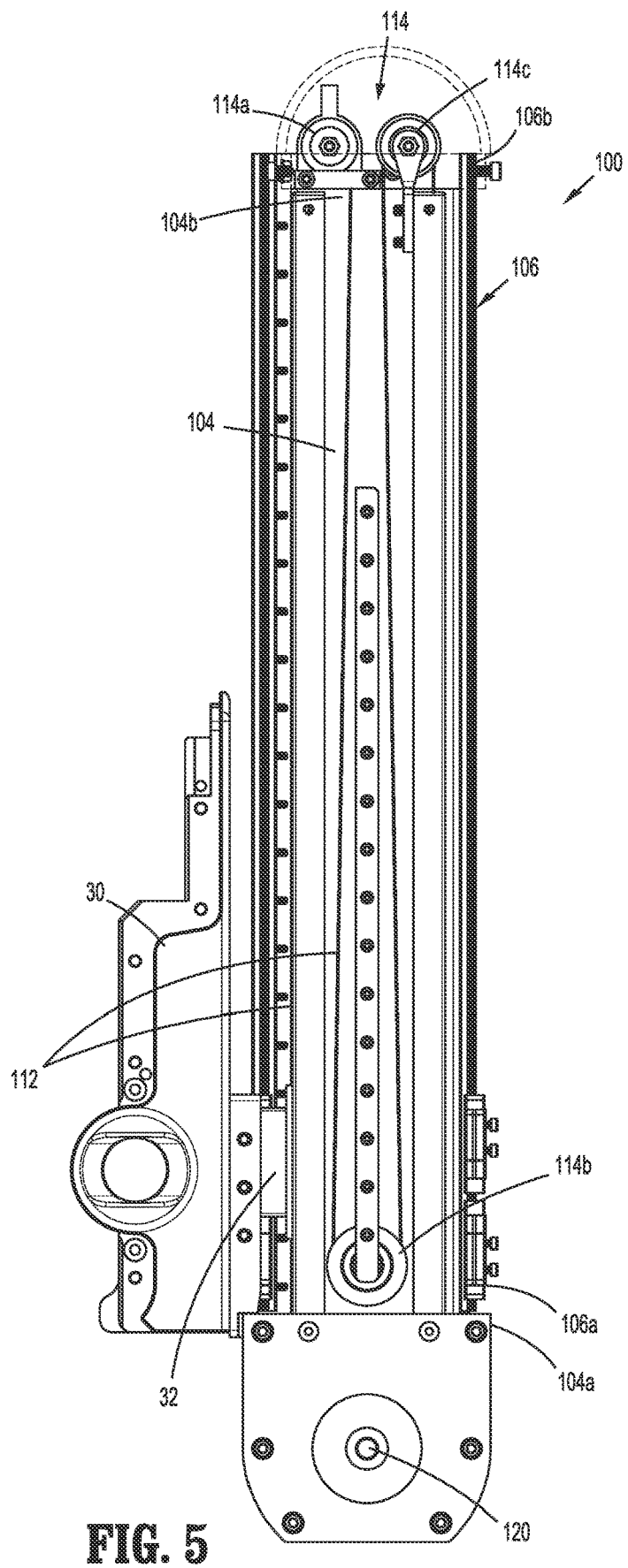
FIG. 5 is a side view of the slide, with an outer shaft of the slide shown in phantom, illustrating an inner shaft of the slide.
Figure 6:
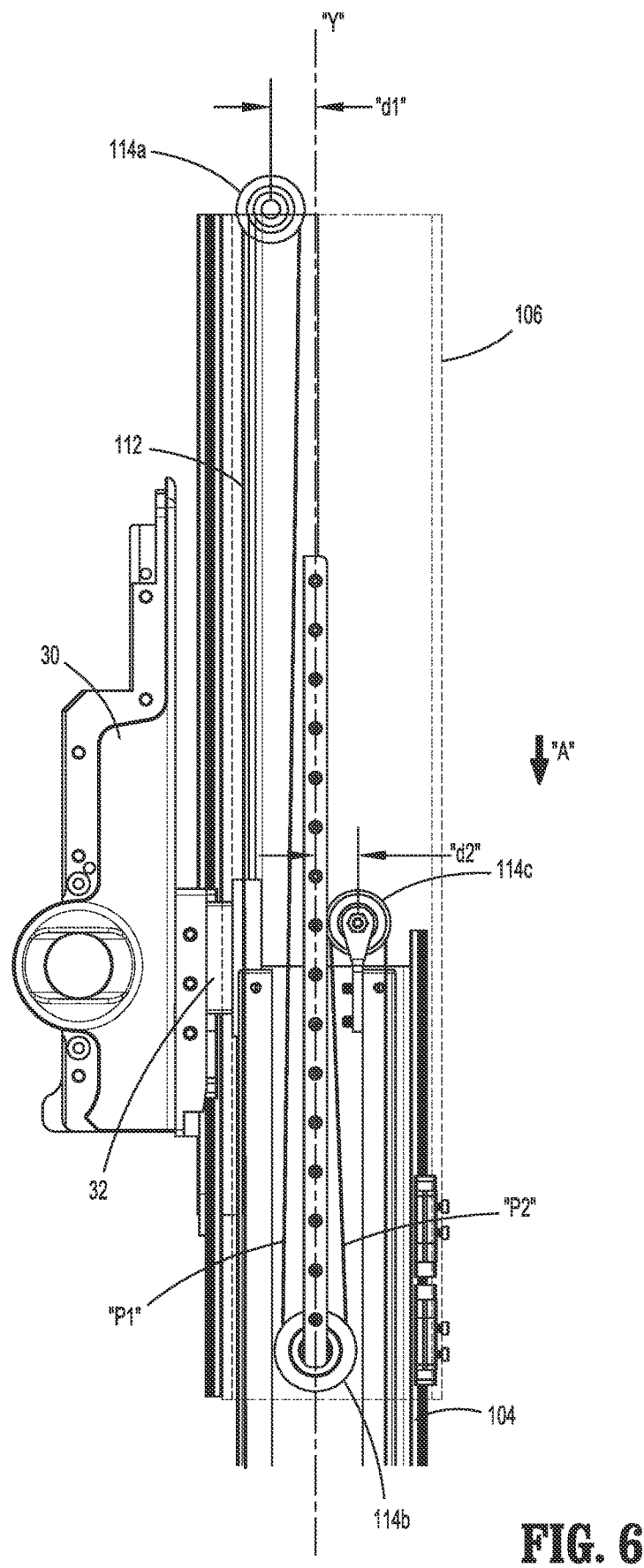
FIG. 6 is a side view of the slide, illustrating a belt and pulley system of the surgical robotic system.

With reference to FIGS. 5-7, the belt and pulley system 114 or drivetrain of the slide 100 is illustrated. The drivetrain 114 is operably coupled to a drive motor 120 disposed in the bottom end portion 104a of the inner shaft 104. The drivetrain 114 includes a pair of first and second pulleys 114a, 114b coupled to the outer shaft 106, and a third pulley 114c coupled to the inner shaft 104. The first pulley 114a is axially fixed and rotatably coupled to the top end portion 106b of the outer sleeve 106 of the slide 100, and the second pulley 114b is axially fixed and rotatably coupled to the bottom end portion 10ba of the outer sleeve 106. As such, as the outer sleeve 106 moves relative to the inner shaft 104 toward the extended position, the first and second pulleys 114a, 114b move therewith. The third pulley 114c is axially fixed and rotatably coupled to the top end portion 104b of the inner shaft 104.

The second pulley 114b is disposed between the first and third pulleys 114a, 114c and is longitudinally spaced from the first pulley 114a along the length of the outer sleeve 106. As shown in FIG. 5, when the outer sleeve 106 is in the retracted position, the first and third pulleys 114a, 114c are disposed adjacent one another, with the second pulley 114b longitudinally spaced from the third pulley 114c. As shown in FIG. 7, when the outer sleeve 106 is in the extended position, the first and third pulleys 114a, 114c are longitudinally spaced from one another, with the second and third pulleys 114b, 114c proximate to one another.

With specific reference to FIG. 6, the second pulley 114b is positioned relative to the first and third pulleys 114a, 114c so that a net downward force, in the direction indicated by arrow "A" in FIG. 6, is exerted on the outer sleeve 106. In particular, the second pulley 114b has a vertical axis "Y" extending through a center point thereof and parallel with the longitudinal axis "X" (FIG. 2) of the inner shaft 104. The first pulley 114a is disposed a first distance "d1" from the vertical axis "Y" in a transverse direction, and the third pulley 114c is disposed a second distance "d2" from the vertical axis "Y" in the transverse direction, less than the first distance "d1." Accordingly, a first portion "P1" of the belt 112 extends from the second pulley 114b to the first pulley 114a at an angle greater than an angle at which a second portion "P2" of the belt 112 extends from the second pulley 114b to the third pulley 114c. Due to the difference in these angles, the downward force exerted by the first pulley 114a on the outer sleeve 106 is greater than the upward force exerted by the third pulley 114c on the outer sleeve 106, whereby the outer sleeve 106 has a constant net downward force imparted thereon. Stated differently, a sum of all of the Y-components of force acting on first portion "P1" of belt 112, and second portion "P2" of belt 112, due to the angles of inclination of first portion "P1" and second portion "P2" of belt 112, is such that there is constant net downward force imparted on outer sleeve 106.

Figure 9:
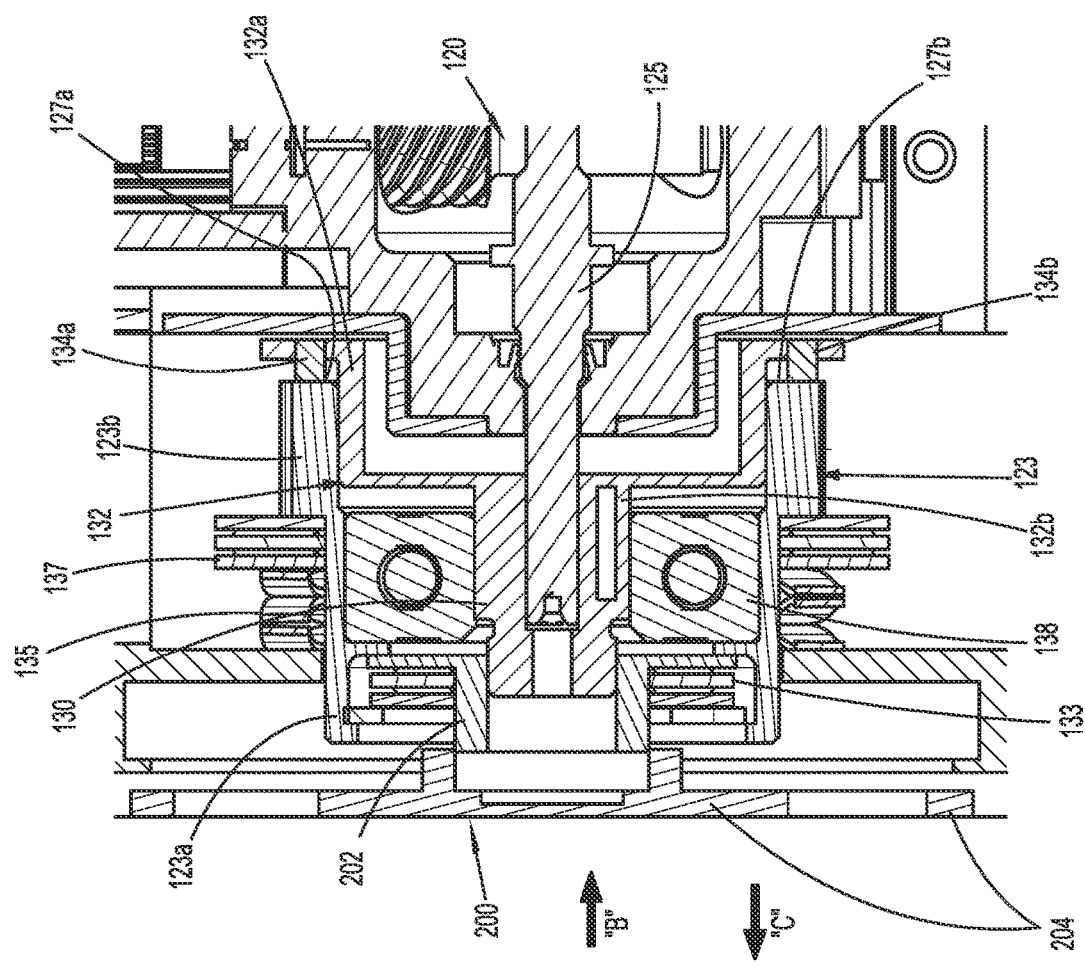
FIG. 9 is a cross-sectional view, taken along line 9-9 in FIG. 8, of components of the motor release mechanism of FIG. 8 and the belt and pulley system of FIG. 6.

The belt 112 is operably coupled to the drive motor 120, via a main pulley 123 (FIG. 9), and each of the first, second, and third pulleys 114a-c. The belt 112 is wrapped over the first pulley 114a, under the second pulley 114b, and over the third pulley 114c. The belt 112 is driven by the motor 120 and is fixed to the coupling member 32 of the carriage 30, such that an activation of the motor 120 causes the belt 112 to move around the pulleys 114a-c and move the attached carriage 30 along the outer sleeve 106 either toward the ascended position or the descended position.

In operation, prior to performing a surgical procedure, the instrument dive unit 20 may be attached to the carriage 30, and the electromechanical instrument 10 may be attached to the instrument drive unit 20. With the instrument drive unit 20 and the associated electromechanical instrument 10 attached to the carriage 30, a longitudinal position (e.g., height) of the carriage 30 along the longitudinal axis "X" may be adjusted. For example, to raise the carriage 30, the motor 120 of the slide 100 is activated to move the belt 112 upwardly relative to the outer sleeve 106 of the slide 100. The carriage 30 is raised to the ascended position and contacts the locking feature 118 and/or the surface feature 116 of the top end portion 106b of the outer sleeve 106. With the carriage 30 fixed to the top end portion 106b of the outer sleeve 106, an activation of the motor 120 causes the carriage 30 to exert an upward force on the outer sleeve 106 to move the outer sleeve 106 upwardly relative to the inner shaft 104. As the outer sleeve 106 moves, the first and second pulleys 114a, 114b move therewith and relative to the third pulley 114c. In the fully extended position, as shown in FIG. 7, the slide 100 assumes a length substantially equal to the length of a conventional slide.

Figure 4:
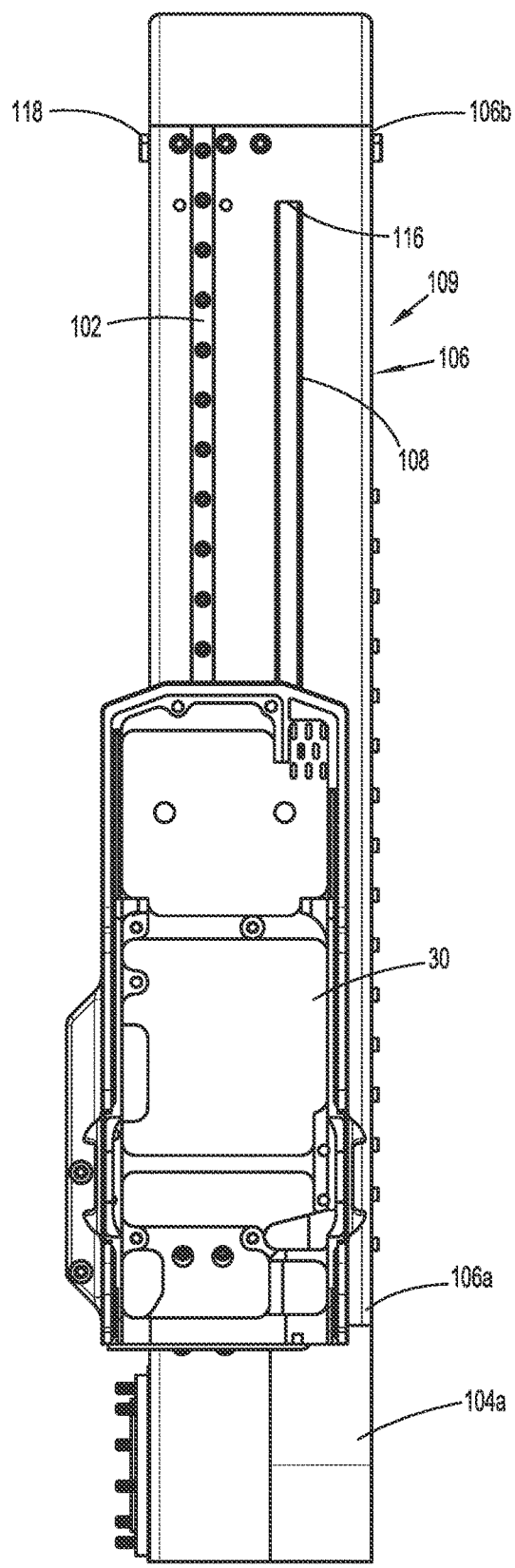
FIG. 4 is a front view, with parts removed, of the carriage coupled to the slide.

To lower the carriage 30 from the extended position, the motor 120 is activated to drive the belt 112 in the opposite direction. In the embodiment where the locking feature 118 fixes the carriage 30 to the top end portion 106b of the outer sleeve 106 of the slide 100, the downward force exerted on the carriage 30, via the belt 112, causes the outer sleeve 106 to retract relative to the inner shaft 104. The outer sleeve 106 may be retracted until the bottom end portion 106a of the outer sleeve 106 bottoms out on the bottom end portion 104a of the inner shaft 104. At this point, to further lower the carriage 30, the belt 112, via the motor 120, exerts a force great enough to unlock the carriage 30 from the top end portion 106a of the outer sleeve 106, whereby the carriage 30 descends along the track 102 of the outer sleeve 106 toward the descended position, as shown in FIGS. 3-5.

With reference to FIGS. 8-10B, the slide 100 may further include a motor release mechanism 200 for manually disengaging the main pulley 123 of the belt and pulley system 114 (FIG. 5) from the drive motor 120 to allow a clinician to manually move the carriage 30 and associated instrument drive unit 20 and surgical instrument 10 to a safe position away from the position during an emergency situation (e.g., a power outage).

The motor release mechanism 200 generally includes a hub 202 and a knob 204. The hub 202 is threadedly coupled to a threaded outer surface 130 of a motor output member 132, and the knob 204 is slidably coupled to the hub 202. The knob 204 protrudes outwardly from the slide 100 to provide access to the knob 204. To activate the motor release mechanism 200, the knob 204 is pushed inwardly, in the direction indicated by arrow "B" in FIG. 9, which non-rotationally fixes the knob 204 to the hub 202 in a friction fit engagement. With the knob 204 non-rotationally fixed to the hub 202, a rotation of the knob 204 rotates the hub 202 relative to the motor output member 132. As the motor release mechanism 200 is rotated, the motor release mechanism 200 is pulled along the motor output member 132, in the direction indicated by arrow "C." In embodiments, the knob 204 may be permanently non-rotatably coupled to the hub 202 to remove the safety step of pushing the knob 204 into engagement with the hub 202 prior to activating the motor release mechanism 200.

The hub 202 of the motor release mechanism 200 is axially retained within a proximal end 123a of the pulley 123 while also being permitted to rotate relative to the pulley 123. A thrust bearing 133 may be provided to facilitate rotation of the hub 202 within and relative to the pulley 132. Due to the hub 202 being axially retained within the pulley 123, as the hub 202 of the motor release mechanism 200 is moved in direction "C," so is the pulley 123.

The motor output member 132 of the belt and pulley system 114 includes a casing 132a and a shaft 132b extending from the casing 132a. The shaft 132b is non-rotationally fixed to a motor gearbox output shaft 125 of the drive motor 120 and extends axially through the pulley 123. A pair of torque transfer pins 134a, 134b are fixed to the casing 132a and extend through corresponding bores 127a, 127b defined through a distal end 123b of the pulley 123. In embodiments, there may be more or less than two pins 134a, 134b. The torque transfer pins 134a, 134b drivingly couple the pulley 123 to the motor output member 132, such that the pulley 123 rotates with the motor output member 132 in response to an activation of the drive motor 120.

Figure 10A:
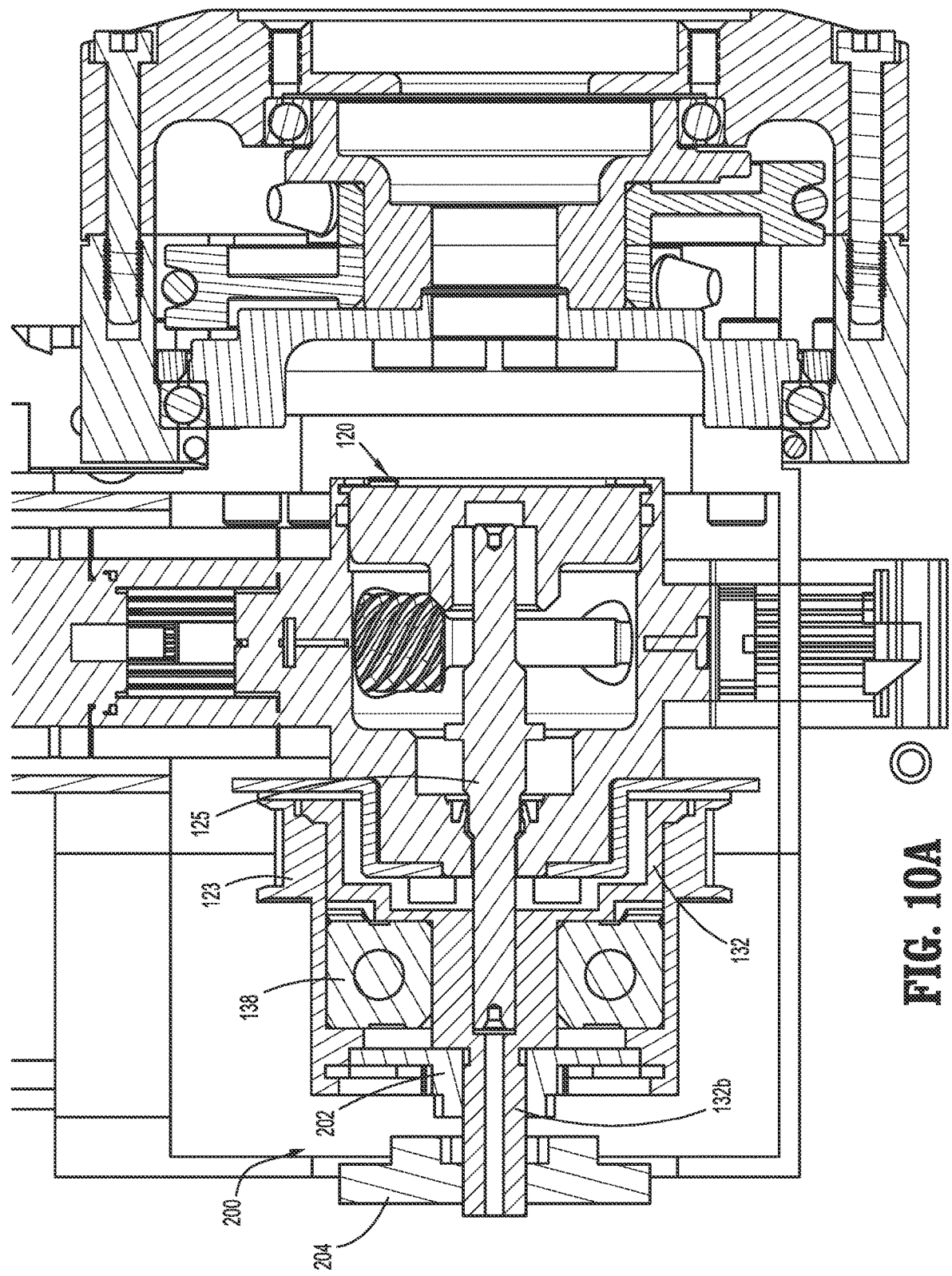
FIG. 10A is a cross-sectional view of components of the motor release mechanism of FIG. 8 and the belt and pulley system of FIG. 6, illustrating the motor release mechanism in an inactivated state.
Figure 10B:
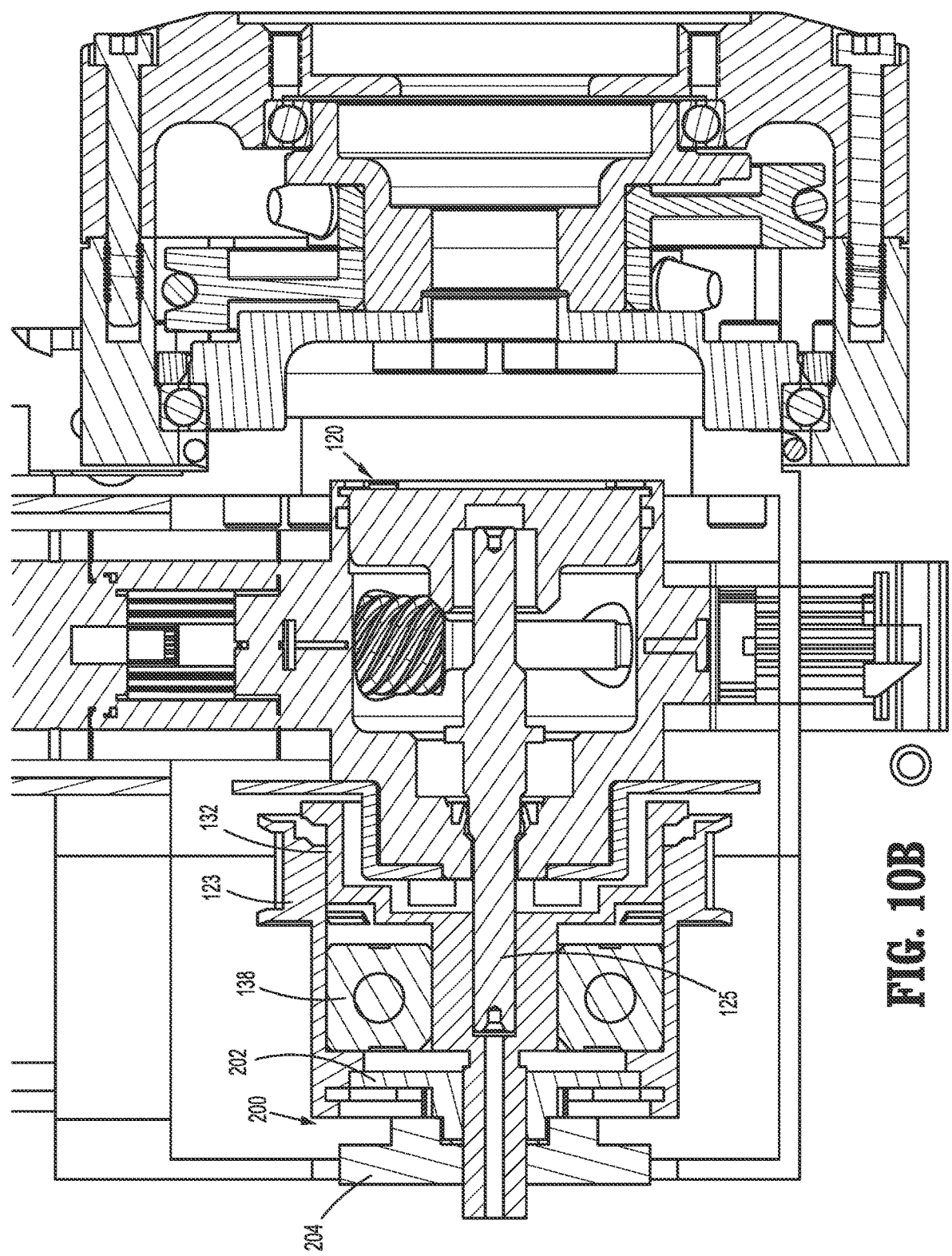
FIG. 10B is a cross-sectional view of components of the motor release mechanism of FIG. 8 and the belt and pulley system of FIG. 6, illustrating the motor release mechanism in an activated state.

The pulley 123 is slidable relative to and along the pins 134a, 134b to adjust an axial position of the pulley 123 relative to the motor output member 132. In particular, the pulley 123 is axially movable along the torque transfer pins 134a, 134b, in response to an activation of the motor release mechanism 200, between a first axial position, as shown in FIG. 10A, and a second axial position, as shown in FIG. 10B. In the first axial position, the torque transfer pins 134a, 134b extend through the bores 127a, 127b of the pulley 123, non-rotationally fixing the pulley 123 with the motor output member 132. In the second axial position, the pulley 123 is disengaged from the torque transfer pins 134a, 134b, whereby the pulley 123 is decoupled from the motor output member 123 and independently rotatable relative to the motor output member 132. The slide 100 may include a spring 135 (e.g., a wave spring) that resiliently biases the pulley 123 toward the first position. A thrust bearing 137 may be provided to facilitate rotation of the pulley 123 relative to the spring 135.

The slide 100 further includes a one way bearing 138 disposed within the pulley 123 and captured between the pulley 123 and the shaft 132b of the motor output member 132. The bearing 138 may be non-rotationally fixed to the shaft 132b of the motor output member 132. The bearing 138 may be any suitable one way bearing or clutch, such as, for example, a one way bearing having rollers, sprags, or spring elements. The bearing 138 is configured to resist rotation of the pulley 123 relative to the motor output member 132 in the direction corresponding to a movement of the carriage 30/instrument drive unit 20 in a downward direction along the slide 100, as described below.

In operation, when the pulley 123 is in the first or operational position, as shown in FIG. 10A, an activation of the drive motor 120 rotates the motor output member 132, the bearing 138, and the pulley 123 as one integral unit in either rotational direction (i.e., clockwise or counter-clockwise). As described above, a rotation of the pulley 123 results in a movement of the surgical instrument 10 along the slide 100 in a selected direction. For example, a clockwise rotation of the pulley 123 may result in an upward movement of the surgical instrument 10 along the slide 100, whereas a counter-clockwise rotation of the pulley 123 may result in a downward movement of the surgical instrument 10 along the slide.

During an emergency (e.g., a power outage), a clinician may desire to move the surgical instrument 10 out of and away from the patient. However, during a power outage, the drive motor 120 will be locked out and prevent a manual movement of the surgical instrument 10 along the slide 100. Accordingly, to move the surgical instrument 10/carriage 30/instrument drive unit 20, the carriage 30 may need to be operably disengaged from the drive motor 120.

To disengage the drive motor 120 from the carriage 20, the motor release mechanism 200 may be actuated by pushing the knob 204 thereof into non-rotational engagement with the hub 202 thereof. With the knob 204 and hub 202 of the motor release mechanism 200 non-rotationally coupled to one another, the knob 204 and hub 202 are rotated together about the motor output member 132 to draw the pulley 123 away from the casing 132a of the motor output member 132 toward the second position, whereby the belt and pulley system 114 (FIG. 5) is disengaged from the drive motor 120.

When the pulley 123 is in the second or safety position, as shown in FIG. 10B, the bearing 138 permits a rotation of the pulley 123 relative thereto and relative to the motor output member 132 in the direction corresponding to movement of the carriage 30/instrument drive unit 20/surgical instrument 10 in an upward direction along the slide 100. Accordingly, the surgical instrument 10 may be manually moved up and out of the patient to a selected position along the slide 100. In contrast, an attempt to move the carriage 30/instrument drive unit 20/surgical instrument 10 in the downward direction is thwarted due to the one way bearing 138 preventing rotation of the pulley 123 relative to the bearing 138 in the corresponding rotational direction. Further, since the drive motor 120 is in a locked state (e.g., due to a power outage), the drive motor 120 prevents the bearing 138 and the motor output member 132 from being rotated by the applied force on the carriage 30/instrument drive unit 20/surgical instrument 10.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A surgical robotic system, comprising:
an elongated slide defining a longitudinal axis;
a carriage for supporting an instrument drive unit, wherein the carriage is coupled to the elongated slide and movable relative thereto along the longitudinal axis;
a drive motor operably coupled to the carriage and configured to drive the movement of the carriage relative to the elongated slide;
a motor release mechanism configured to selectively disengage the drive motor from the carriage to permit a manual movement of the carriage along the elongated slide;
a pulley operably coupling the drive motor and the carriage, wherein an activation of the motor release mechanism disengages the pulley from the drive motor; and
a motor output member rotatable by the drive motor, wherein an activation of the motor release mechanism slides the pulley relative to the motor output member from a first position, in which the pulley and the motor output member are rotatable with one another, to a second position, in which the pulley is independently rotatable relative to the motor output member.

2. The surgical robotic system according to claim 1, further comprising at least one torque transfer pin non-rotatably coupling the pulley with the motor output member, wherein the pulley is configured to slide between the first and second positions along the at least one torque transfer pin.

3. The surgical robotic system according to claim 1, further comprising a one way bearing disposed between the pulley and the motor output member, wherein the one way bearing is configured to allow rotation of the pulley relative to the motor output member in a first direction, and resist rotation of the pulley relative to the motor output member in a second direction.

4. The surgical robotic system according to claim 3, wherein the one way bearing is disposed within the pulley and the motor output member extends through the one way bearing and the pulley.

5. The surgical robotic system according to claim 3, wherein the one way bearing is non-rotationally fixed to the motor output member.

6. The surgical robotic system according to claim 1, wherein the motor release mechanism includes a hub axially retained with the pulley and threadedly coupled to the motor output member, such that a rotation of the hub moves the pulley relative to the motor output member between the first and second positions.

7. The surgical robotic system according to claim 6, wherein the motor release mechanism further includes a knob configured to slide into and out of non-rotatable engagement with the hub.

8. The surgical robotic system according to claim 1, further comprising a belt operably coupled to the pulley and fixed to the carriage, such that movement of the belt drives a movement of the carriage along the elongated slide.

9. The surgical robotic system according to claim 1, further comprising a robotic arm having the elongated slide coupled thereto.

10. A surgical robotic system, comprising:
a robotic arm;
an elongated slide coupled to an end portion of the robotic arm;
a drive motor;
a pulley operably coupled to the drive motor and configured to drive a movement of an instrument drive unit along the elongated slide;
a motor release mechanism configured to selectively disengage the pulley from the drive motor to permit a manual rotation of the pulley relative to the drive motor; and
a motor output member rotatable by the drive motor, wherein an activation of the motor release mechanism slides the pulley relative to the motor output member from a first position, in which the pulley and the motor output member are rotatable with one another, to a second position, in which the pulley is independently rotatable relative to the motor output member.

11. The surgical robotic system according to claim 10, further comprising at least one torque transfer pin non-rotatably coupling the pulley with the motor output member, wherein the pulley is configured to slide between the first and second positions along the at least one torque transfer pin.

12. The surgical robotic system according to claim 10, further comprising a one way bearing disposed between the pulley and the motor output member, wherein the one way bearing is configured to allow rotation of the pulley relative to the motor output member in a first direction, and resist rotation of the pulley relative to the motor output member in a second direction.

13. The surgical robotic system according to claim 12, wherein the one way bearing is disposed within the pulley and the motor output member extends through the one way bearing and the pulley.

14. The surgical robotic system according to claim 12, wherein the one way bearing is non-rotationally fixed to the motor output member.

15. The surgical robotic system according to claim 10, wherein the motor release mechanism includes a hub axially retained with the pulley and threadedly coupled to the motor output member, such that a rotation of the hub moves the pulley relative to the motor output member between the first and second positions.

16. The surgical robotic system according to claim 15, wherein the motor release mechanism further includes a knob configured to slide into and out of non-rotatable engagement with the hub.

17. The surgical robotic system according to claim 10, further comprising a belt operably coupled to the pulley and fixedly coupled to an instrument drive unit, such that movement of the belt drives a movement of an instrument drive unit along the elongated slide.

* * * * *